United States Patent [19]
Pelrine et al.

[11] Patent Number: 4,926,004
[45] Date of Patent: May 15, 1990

[54] REGENERATION OF REDUCED SUPPORTED CHROMIUM OXIDE CATALYST FOR ALPHA-OLEFIN OLIGOMERIZATION

[75] Inventors: Bruce P. Pelrine, Trenton; Margaret M. Wu, Belle Mead, both of N.J.

[73] Assignee: Mobil Oil Corporation, New York, N.Y.

[21] Appl. No.: 282,362

[22] Filed: Dec. 9, 1988

[51] Int. Cl.[5] .................... C07C 2/02
[52] U.S. Cl. .................... 585/530; 585/10
[58] Field of Search .................... 585/10, 530

[56] References Cited

U.S. PATENT DOCUMENTS

| | | | |
|---|---|---|---|
| 2,825,721 | 3/1958 | Hogan et al. | 585/530 |
| 4,827,064 | 5/1989 | Wu | 585/10 |
| 4,827,073 | 5/1989 | Wu | 585/530 |

*Primary Examiner*—Curtis R. Davis
*Attorney, Agent, or Firm*—Alexander J. McKillop; Charles J. Speciale; Malcolm D. Keen

[57] ABSTRACT

A process for producing liquid oligomers useful as lubricants from alpha-olefins feedstock, such as 1-decene. The olefins are oligomerized over a supported and reduced metal oxide catalyst from Group VIB of the Periodic Table to produce the oligomers. The chromium-on-silica oligomerization catalysts can be regenerated to allow repeated recycling of the catalyst with reduced losses in yield of the lubricant. The regeneration process is particularly useful to regenerate catalyst deactivated during the course of oligomerization at high temperatures to produce low viscosity HVI-PAO lubricant. The regeneration process is carried out by (i) purging the deactivated catalyst with inert gas to strip unreacted olefin and lubricant product; (ii) contacting the purged catalyst with a stream of oxidizing gas at an elevated temperature to oxidize the carbonaceous deposits; and (iii) cooling the catalyst and contacting it with a stream of reducing gas to reduce the metal component to a lower valence state.

12 Claims, 1 Drawing Sheet

PRODUCT YIELD VS REGENERATIONS

PRODUCT YIELD, WEIGHT PERCENT

CHROMIUM/SILICA EXTRUDATE
○: TEMPERATURE = 125 C (100 CS)
□: TEMPERATURE = 180 C (12 CS)

CATALYST AGING - 100 CS PRODUCT YIELD
YIELD, WEIGHT PERCENT
100
90
80
70
60
50
40
30
20
10
0
2 6 10 14 18 22 26 30 34 38 42 46 50 54 58 62
CHROMIUM/SILICA EXTRUDATE
○ = 0.5 WHSV
▯ = 2.2 WHSV
SECOND (2 ND) CYCLE

PRODUCT YIELD VS REGENERATIONS
PRODUCT YIELD, WEIGHT PERCENT
100
90
80
70
60
50
40
30
20
10
0
0 1 2 3 4 5
CHROMIUM/SILICA EXTRUDATE
○: TEMPERATURE = 125 C (100 CS)
▯: TEMPERATURE = 180 C (12 CS)

REGENERATION OF REDUCED SUPPORTED CHROMIUM OXIDE CATALYST FOR ALPHA-OLEFIN OLIGOMERIZATION

This invention relates to novel processes for the production of lubricant compositions. The invention, more particularly, relates to novel synthetic lubricant compositions prepared from alpha-olefins, or 1-alkenes, and their method of preparation. The invention specifically relates to novel processes for the regeneration of reduced chromium catalyst used in the fixed bed preparation of the novel lubricant compositions.

BACKGROUND OF THE INVENTION

Catalytic oligomerization of olefins is a known technique for manufacturing hydrocarbon basestocks useful as lubricants. Efforts to improve upon the performance of natural mineral oil based lubricants by the synthesis of oligomeric hydrocarbon fluids have been the subject of important research and development in the petroleum industry for many years and have led to the relatively recent market introduction of a number of superior polyalpha-olefin (PAO) synthetic lubricants, primarily based on the oligomerization of alpha-olefins or 1-alkenes. In terms of lubricant property improvement, the thrust of the industrial research effort on synthetic lubricants has been toward fluids exhibiting useful viscosities over a wide range of temperature, i.e., improved viscosity index (VI), while also showing lubricity, thermal and oxidative stability and pour point equal to or better than mineral oil. These new synthetic lubricants lower friction and hence increase mechanical efficiency across the full spectrum of mechanical loads from worm gears to traction drives and do so over a wider range of operating conditions than mineral oil lubricants.

The chemical focus of the research effort in synthetic lubricants has been on the polymerization of 1-alkenes. Well known structure/property relationships for high polymers as contained in the various disciplines of polymer chemistry have pointed the way to 1-alkenes as a fruitful field of investigation for the synthesis of oligomers with the structure thought to be needed to confer improved lubricant properties thereon. Due largely to studies on the polymerization of propene and vinyl monomers, the mechanism of the polymerization of 1-alkene and the effect of that mechanism on polymer structure is reasonably well understood, providing a strong resource for targeting on potentially useful oligomerization methods and oligomer structures. Building on that resource, in the prior art oligomers of 1-alkenes from $C_6$ to $C_{20}$ have been prepared with commercially useful synthetic lubricants from 1-decene oligomerization yielding a distinctly superior lubricant product via either cationic or Ziegler catalyzed polymerization.

One characteristic of the molecular structure of 1-alkene oligomers that has been found to correlate very well with improved lubricant properties in commercial synthetic lubricants is the ratio of methyl to methylene groups in the oligomer. The ratio is called the branch ratio and is calculated from infra red data as discussed in "Standard Hydrocarbons of High Molecular Weight'-',*Analytical Chemistry.* Vol. 25, No. 10, p. 1466 (1953). Viscosity index has been found to increase with lower branch ratio. Heretofore, oligomeric liquid lubricants exhibiting very low branch ratios have not been synthesized from 1-alkenes. For instance, oligomers prepared from 1-decene by either cationic polymerization or Ziegler catalyst polymerization have branch ratios of greater than 0.20. Shubkin, *Ind. Eng. Chem. Prod. Res. Dev.* 1980, 19, 15–19, provides an explanation for the apparently limiting value for branch ratio based on a cationic polymerization reaction mechanism involving rearrangement to produce branching. Other explanations suggest isomerization of the olefinic group in the one position to produce an internal olefin as the cause for branching. Whether by rearrangement, isomerization or a yet to be elucidated mechanism it is clear that in the art of 1-alkene oligomerization to produce synthetic lubricants as practiced to-date excessive branching occurs and constrains the limits of achievable lubricant properties, particularly with respect to viscosity index. Obviously, increased branching increases the number of isomers in the oligomer mixture, orienting the composition away from the structure which would be preferred from a consideration of the theoretical concepts discussed above.

Recently, novel lubricant compositions (referred to herein as HVI-PAO and the HVI-PAO process) comprising polyalpha-olefins and methods for their preparation employing as catalyst reduced chromium on a silica support have been disclosed in U.S. patent applications Ser. No. 210,434 and 210,435 filed June 23, 1988, incorporated herein by reference. The process comprises contacting $C_6$–$C_{20}$ 1-alkene feedstock with reduced valence state chromium oxide catalyst on porous silica support under oligomerizing conditions in an oligomerization zone whereby high viscosity, high VI liquid hydrocarbon lubricant is produced having branch ratios less than 0.19 and pour point below $-15°$ C. Lubricants produced by the process cover the full range of lubricant viscosities and exhibit a remarkably high VI and low pour point even at high viscosity.

In the HVI-PAO process to prepare unique lubricant oligomeric compositions having high viscosity index, oligomerization in a fixed bed reactor provides certain economic and process control advantages not readily achievable through other reactor and process configurations. However, the feasibility of fixed bed catalytic processing of 1-alkenes to prepare HVI-PAO lubricants depends upon an effective process for catalyst regeneration that will permit multiple regeneration cycles without significant loss in product yield or diminution of the unusual properties of HVI-PAO lubricants. Prior art processes for the polymerization of 1-alkene using catalyst similar to, although not identical to, the catalyst used in the HVI-PAO process were directed to high polymer preparation using very low concentration of catalyst. Hence, catalyst regeneration was not a requirement for process feasibility and a teaching directly pertinent to regeneration of HVI-PAO catalyst in a fixed bed reactor has not been made.

Accordingly, it is an object of the instant invention to provide a process for the regeneration of HVI-PAO process catalyst.

It is a further object of the present invention to provide a catalyst regeneration process for HVI-PAO process which will allow multiple regeneration cycles without significant loss in product yield of properties.

A particular object of the instant invention is to provide a process for the regeneration the HVI-PAO catalyst comprising reduced chromium oxide on porous support.

SUMMARY OF THE INVENTION

An improved process incorporating catalyst regeneration has been discovered to produce liquid oligomers from alpha-olefins feedstock, such as 1-decene, wherein said oligomers have branch ratios below 0.19 and have higher viscosity indices than oligomers with higher branch ratios. The olefins can be oligomerized over a supported and reduced metal oxide catalyst from Group VIB of the Periodic Table to give oligomers suitable for lubricant application. It has been found that in the oligomerization of the olefins using a chromium on silica catalyst the catalyst can be regenerated to allow repeated recycling of the catalyst without a loss in yield of the HVI-PAO lubricant. Further, it has been found that the regeneration process is particularly useful to regenerate catalyst deactivated during the course of oligomerization at high temperatures to produce low viscosity HVI-PAO lubricant.

More particularly, in a process for the preparation of liquid hydrocarbons suitable as lubricant basestocks from alpha-olefin feedstock containing 6 to 20 carbon atoms, or mixtures of such olefins, comprising contacting said olefins under oligomerization conditions, at reaction temperature between 90° to 250° C. to vary product viscosity, and with a chromium catalyst on a porous support, which catalyst has been treated by oxidation at a temperature of 200° C. to 900° C. in the presence of an oxidizing gas and then by treatment with a reducing agent at a temperature and for a time sufficient to reduce said catalyst to a lower valence state to obtain an oligomeric liquid lubricant composition comprising $C_{30}$–$C_{1300}$ hydrocarbons, said composition having a branch ratio of less than 0.19, weight average molecular weight between 420 and 45,000, number average molecular weight between 420 and 18,000, molecular weight distribution between 1 and 5 and pour point below −15° C., the improvement comprising; regenerating deactivated chromium catalyst in a process comprising the steps of: stripping said deactivated catalyst with inert gas at elevated temperature; contacting said deactivated catalyst with oxidizing gas while raising the catalyst temperature and holding said temperature for a time sufficient to oxidize said catalyst to hexavalent chromium and remove carbonaceous deposits; cooling said hexavalent chromium catalyst and contacting with carbon monoxide at a temperature and for a time sufficient to reduce said hexavalent chromium to divalent chromium.

DETAILED DESCRIPTION OF THE INVENTION

Figure 1:
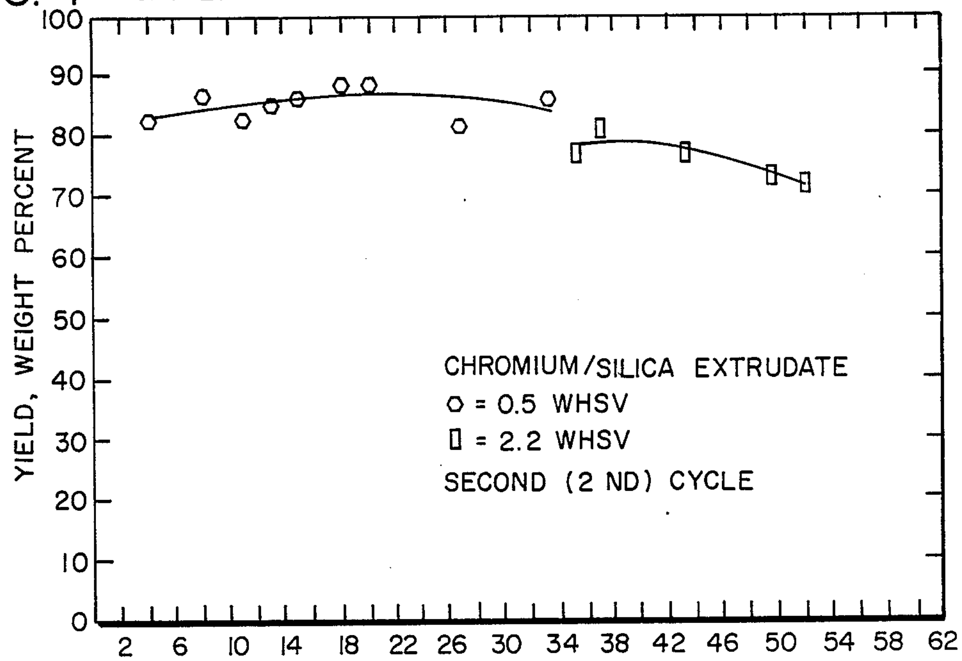
FIG. 1 is a plot of catalyst aging versus time-on stream for the second cycle of HVI-PAO process.

In the following description, unless otherwise stated, all references to HVI-PAO oligomers or lubricants refer to hydrogenated oligomers and lubricants in keeping with the practice well known to those skilled in the art of lubricant production. As oligomerized, HVI-PAO oligomers are mixtures of dialkyl vinylidenic and 1,2 dialkyl or trialkyl monoolefins. Lower molecular weight unsaturated oligomers are preferably hydrogenated to produce thermally and oxidatively stable, useful lubricants. Higher molecular weight unsaturated HVI-PAO oligomers are sufficiently thermally stable to be utilized without hydrogenation and, optionally, may be so employed. Both unsaturated and hydrogenated HVIPAO of lower or higher molecular exhibit viscosity indices of at least 130 and pour point below −15° C.

The prior art process described herein to produce the novel HVI-PAO oligomers can be controlled by varying oligomerization temperature to yield oligomers having weight average molecular weight between 300 and 45,000 and number average molecular weight between 300 and 18,000. Measured in carbon numbers, molecular weights range from $C_{30}$ to $C_{1300}$ and viscosity up to 750 cs at 100° C., with a preferred range of $C_{30}$ to $C_{1000}$ and a viscosity of up to 500 cs at 100° C. Molecular weight distributions (MWD), defined as the ratio of weight average molecular to number average molecular weight, range from 1.00 to 5, with a preferred range of 1.01 to 3 and a more preferred MWD of about 1.05 to 2.5. Compared to conventional PAO derived from $BF_3$ or $AlC_3$ catalyzed polymerization of 1-alkene, HVI-PAO has been found to have a higher proportion of higher molecular weight polymer molecules in the product.

Viscosities of the novel HVI-PAO oligomers measured at 100° C. range from 3 cS to 5000 cS. The viscosity index for the new polyalpha-olefins is approximately described by the following equation:

$$VI = 156.8 + 4.94 \times (V_{100°C.})^{0.5},$$

where $V_{100°C.}$ is kinematic viscosity in centistokes measured at 100° C.

Olefins suitable for use as starting material in the preparation of HVI-PAO include those olefins containing from 2 to about 20 carbon atoms such as ethylene, propylene, 1-butene, 1-pentene, 1-hexene, 1-octene, 1-decene, 1-dodecene and 1-tetradecene and branched chain isomers such as 4-methyl-1-pentene. Also suitable for use are olefin-containing refinery feedstocks or effluents. However, the olefins used in this invention are preferably alpha olefinic as for example 1-heptene to 1-hexadecene and more preferably 1-octene to 1-tetradecene, or mixtures of such olefins.

Oligomers of alpha-olefins in accordance with the invention have a low branch ratio of less than 0.19 and superior lubricating properties compared to the alpha-olefin oligomers with a high branch ratio, as produced in all known commercial methods.

This new class of alpha-olefin oligomers are prepared by oligomerization reactions in which a major proportion of the double bonds of the alpha-olefins are not isomerized. These reactions include alpha-olefin oligomerization by supported metal oxide catalysts, such as Cr compounds on silica or other supported IUPAC Periodic Table Group VIB compounds. The catalyst most preferred is a lower valence Group VIB metal oxide on an inert support. Preferred supports include silica, alumina, titania, silica alumina, magnesia and the like. The support material binds the metal oxide catalyst. Those porous substrates having a pore opening of at least 40 angstroms are preferred.

The support material usually has high surface area and large pore volumes with average pore size of 40 to about 350 angstroms. The high surface area are beneficial for supporting large amount of highly dispersive, active chromium metal centers and to give maximum efficiency of metal usage, resulting in very high activity catalyst. The support should have large average pore openings of at least 40 angstroms, with an average pore opening of >60 to 300 angstroms preferred. This large pore opening will not impose any diffusional restriction of the reactant and product to and away from the active catalytic metal centers, thus further optimizing the catalyst productivity. Also, for this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, $H_2$, $NH_3$, $H_2S$, $CS_2$, $CH_3SCH_3$, $CH_3SSCH_3$, metal alkyl containing compounds such as $R_3Al$, $R_3B$,$R_2Mg$, RLi, $R_2Zn$, where R is alkyl, alkoxy, aryl and the like. Preferred are CO or $H_2$ or metal alkyl containing compounds. Alternatively, the Group VIB metal may be applied to the substrate in reduced form, such as CrII compounds. The resultant catalyst is very active for oligomerizing olefins at a temperature range from below room temperature to about 250° C. at a pressure of 0.1 atmosphere to 5000 psi. Contact time of both the olefin and the catalyst can vary from one second to 24 hours. The catalyst can be used in a batch type reactor or in a fixed bed, continuous-flow reactor.

In general the support material may be added to a solution of the metal compounds, e.g., acetates or nitrates, etc., and the mixture is then mixed and dried at room temperature. The dry solid gel is purged with air at successively higher temperatures to about 600° for a period of about 16 to 20 hours. Thereafter the catalyst is cooled down under an inert atmosphere to a temperature of about 250° to 450° C. and a stream of reducing agent such as CO or $H_2$ is contacted therewith for a period to reduce the catalyst as indicated by a distinct color change from bright orange to bluish green. Typically, the catalyst is treated with an amount of CO equivalent to a two-fold stoichiometric excess to reduce the catalyst to a lower valence CrII state. Finally the catalyst is cooled down to room temperature and is ready for use.

The product oligomers have a very wide range of viscosities with high viscosity indices suitable for high performance lubrication use. The product oligomers also have a tactic molecular structure of mostly uniform head-to tail connections with some head-to-head type connections in the structure. These low branch ratio oligomers have high viscosity indices at least about 15 to 20 units and typically 30–40 units higher than equivalent viscosity prior art oligomers, which regularly have higher branch ratios and correspondingly lower viscosity indices. These low branch oligomers maintain better or comparable pour points.

The branch ratios defined as the ratios of $CH_3$ groups to $CH_2$ groups in the lube oil are calculated from the weight fractions of methyl groups obtained by infrared methods, published in *Analytical Chemistry*, Vol. 25, No. 10, p. 1466 (1953).

$$\text{Branch ratio} = \frac{\text{wt fraction of methyl group}}{1 - (\text{wt fraction of methyl group})}$$

The following examples of the preparation of HVI-PAO oligomers are presented merely for illustration purposes and are not intended to limit the scope of the present invention.

EXAMPLE 1

Catalyst Preparation and Activation Procedure 1.9 grams of chromium (II) acetate ($Cr_2(OCOCH_3)_4 2H_2O$)(5.58 mmole) (commercially obtained) is dissolved in 50 cc of hot acetic acid. Then 50 grams of a silica gel of 8–12 mesh size, a surface area of 300 $m^2$/g, and a pore volume of 1 cc/g, also is added. Most of the solution is absorbed by the silica gel. The final mixture is mixed for half an hour on a rotor at room temperature and dried in an open-dish at room temperature. First, the dry solid (20 g) is purged with $N_2$ at 250° C. in a tube furnace. The furnace temperature is then raised to 400° C. for 2 hours. The temperature is then set at 600° C. with dry air purging for 16 hours. At this time the catalyst is cooled down under $N_2$ to a temperature of 300° C. Then a stream of pure CO (99.99% from Matheson) is introduced for one hour. Finally, the catalyst is cooled down to room temperature under $N_2$ and ready for use.

EXAMPLE 2

The powdered catalyst prepared in Example 1 (3.2 g ) is packed in a ⅜" stainless steel tubular reactor inside an $N_2$ blanketed dry box. The reactor under $N_2$ atmosphere is then heated to 150° C. by a single-zone Lindberg furnace. Prepurified 1-hexene is pumped into the reactor at 140 psi and 20 cc/hr. The liquid effluent is collected and stripped of the unreacted starting material and the low boiling material at 0.05 mm Hg. The residual clear, colorless liquid has viscosities and VI's suitable as a lubricant base stock.

| Sample | Prerun | 1 | 2 | 3 |
|---|---|---|---|---|
| T.O.S., hr. | 2 | 3.5 | 5.5 | 21.5 |
| Lube Yield, wt % | 10 | 41 | 74 | 31 |
| Viscosity, cs, at | | | | |
| 40° C. | 208.5 | 123.3 | 104.4 | 166.2 |
| 100° C. | 26.1 | 17.1 | 14.5 | 20.4 |
| VI | 159 | 151 | 142 | 143 |

The experiments conducted under the above condition of essentially constant temperature and WHSV produce HVI-PAO with about the same viscosity.

EXAMPLE 3

Similar to Example 2, a fresh catalyst sample is charged into the reactor and 1-hexene is pumped to the reactor at 1 atm and 10 cc per hour. As shown below, a lube of high viscosities and high VI's is obtained. These runs show that at different reaction conditions, a lube product of high viscosities can be obtained and that viscosity can be varied with change in reaction temperature.

| Sample | A | B |
|---|---|---|
| T.O.S., hrs. | 20 | 44 |
| Temp., °C. | 100 | 50 |

-continued

| Sample | A | B |
|---|---|---|
| Lube Yield, % | 8.2 | 8.0 |
| Viscosities, cS at | | |
| 40° C. | 13170 | 19011 |
| 100° C. | 620 | 1048 |
| VI | 217 | 263 |

EXAMPLE 4

A commercial chrome/silica catalyst which contains 1% Cr on a large-pore volume synthetic silica gel is used. The catalyst is first calcined with air at 800° C. for 16 hours and reduced with CO at 300° C. for 1.5 hours. Then 3.5 g of the catalyst is packed into a tubular reactor and heated to 100° C. under the $N_2$ atmosphere. 1-Hexene is pumped through at 28 cc per hour at 1 atmosphere. The products are collected and analyzed as follows:

| Sample | C | D | E | F |
|---|---|---|---|---|
| T.O.S., hrs. | 3.5 | 4.5 | 6.5 | 22.5 |
| Lube Yield, % | 73 | 64 | 59 | 21 |
| Viscosity, cS, at | | | | |
| 40° C. | 2548 | 2429 | 3315 | 9031 |
| 100° C. | 102 | 151 | 197 | 437 |
| VI | 108 | 164 | 174 | 199 |

These runs show that different Cr on a silica catalyst are also effective for oligomerizing olefins to lube products.

EXAMPLE 5

As in Example 4, purified 1-decene is pumped through the reactor at 250 to 320 psi. The product is collected periodically and stripped of light products boiling points below 650° F. High quality lubes with high VI are obtained (see following table). The table also shows that at about the same WHSV, the viscosity of the product decreases with increasing reaction temperature (135°, 166°, 197° C.)

| Reaction Temp., °C. | WHSV g/g/hr | Lube Product Properties | | |
|---|---|---|---|---|
| | | V at 40° C. | V at 100° C. | VI |
| 120 | 2.5 | 1555.4 cs | 157.6 cs | 217 |
| 135 | 0.6 | 389.4 | 53.0 | 202 |
| 150 | 1.2 | 266.8 | 36.2 | 185 |
| 166 | 0.6 | 67.7 | 12.3 | 181 |
| 197 | 0.5 | 21.6 | 5.1 | 172 |

During the production of synthetic lubricants made by reaction of 1-alkenes such as 1-decene over a chromium on silica catalyst, catalyst deactivation occurs especially at higher reaction temperatures. This results in increasingly lower yields with time-on-stream. The yield of product reaches a point where it is not practical to continue the run. Therefore catalyst must be regenerated and restored to its original activity.

FIG. 1 shows a plot of catalyst aging expressed as time on stream compared to product yield for the second cycle preparation of 100 cS (100° C.) HVI-PAO. Over the two month period a slight decrease in activity is noted. For the extruded catalyst a value of 0.4 is found by best fit of the data for the period between 20 to 52 days on stream. A somewhat greater rate of catalyst deactivation is experienced with a powdered catalyst.

In the following examples the process of the instant invention for the regeneration of HVI-PAO process catalyst.

EXAMPLE 6

A. Catalyst Preparation 33 grams of 1/16 inch (1.59 mm) silica extrudates is placed into a 200 ml beaker. A solution of 1.52 grams of chromium acetate in 80 ml of water is added to the extrudates and allowed to sand overnight at room temperature. The excess water is removed by heating until the extrudates are damp. The damp extrudates are then placed into a rotovap at 80° C., under vacuum, and taken to dryness. Additional drying is made by vacuum drying at 120° C. The resulting catalyst is described as follows:

| | |
|---|---|
| Catalyst Diameter, mm | 1.59 |
| Catalyst Length, mm | 6.35 |
| Surface Area, sq. M/Gm | 200 |
| Pore Diameter, Angstroms | 200 |
| Chromium Loading, wt. % | 1.09 |
| Bulk Density, Gm/cc | 0.42 |

10 grams (23 ml) of the above catalyst is placed into a stainless steel, fixed bed reactor whose inside diameter is ⅝ inches (15.9 mm). The length of the catalyst bed is six inches. The interstitial spaces between the extrudates is packed with 70/80 mesh sand. The chromium on silica extrudate catalyst is activated by predrying with dry nitrogen at 250° C., overnight. The catalyst bed is then calcined in air, at 200 cc/min, from 250° to 600° C., at 1° C./minute and held at 600° C. for 12 hours. At the end of 12 hours, the temperature is reduced to 350° C. At this temperature, carbon monoxide, at 200 cc/min, is contacted with the catalyst for 30 minutes to reduce the chromium.

C. Pretreatment of 1-alkene

Prior to contacting the catalyst with the feed, the 1-alkene, such as 1-decene, is treated to remove catalyst poisons. The treatment consists of passing the feed over activated molecular sieves to remove traces of water and polar compounds such as decanol. The feed is further contacted with a reduced copper/chroma catalyst to remove peroxides. A final contact with predried 5A sieves is made. The feed pretreatment is made on a continuous basis before the feed enters the fixed bed reactor.

Example 7

10 grams of the above activated extruded silica catalyst containing 1.09 wt % chromium is placed into a fixed bed reactor. Synthetic HVI-PAO lubricants are then produced by feeding 1-decene to the catalyst bed at 125° C. reactor temperature and weight hourly space velocity (WHSV) based on catalyst of 2.2. Five reaction cycles are preformed with four regenerations between the cycles over a period of four months. The regeneration conditions and results are summarized in Table 1.

TABLE 1

Regeneration Study- Chromium on Silica Extrudate

1. Oligomerization conditions- reactor temperature 125° C. and WHSV of 2.2.

2. Regeneration Conditions: Purge bed with nitrogen at 125° C. for one hour. Ramp temperature to 500° C. and hold for 12 hours. In air, heat from 100° C. to 600° C. @ 1° C./min and hold for 12 hours. Cool to 350° C. and contact catalyst bed with carbon monoxide @ 350° C. and 200 cc/min for 45 minutes.

3. Regeneration results: Run length- four months.

| Cycle | Product Yield, Wt % |
|---|---|
| 1 | 54.0 |
| 2 | 80.0 |
| 3 | 91.0 |
| 4 | 85.0 |
| 5 | 95.0 |

The purpose of the initial nitrogen purge and stripping at high temperatures is to remove as much 1-decene feed and product as possible prior to the air treatment step. The next step in the regeneration is to contact the chromium catalyst with a stream of air while raising the catalyst bed temperature from 100° C. to 600° C. at one degree per minute and holding the 600° C. temperature for 12 hours. The air contacting effectively removes any carbonaceous material from the catalyst and converts the chromium to a +6 (hexavalent) oxidation state. The last step in the regeneration is to cool the bed temperature to 350° C. while purging the be with dry nitrogen. Once a bed temperature of 350° C. is achieved, carbon monoxide is introduced to the catalyst bed to reduce the chromium to the +2 (divalent) oxidation state and thereby reactivate the catalyst for further oligomerization of 1-decene to synthetic lubricant.

The time and temperature of the regeneration conditions in the above example are given only by way of example and are not intended to be limiting.

Figure 2:
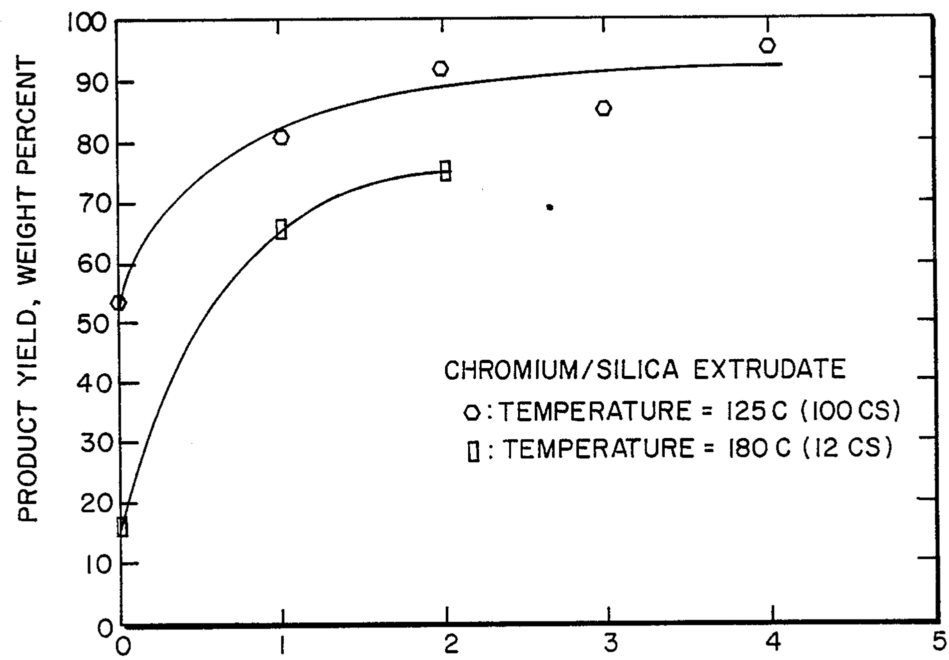
FIG. 2 is a plot of the relationship between product yield and number of catalyst regenerations.

FIG. 2 shows a plot of product yield versus the number of regenerations for the above example and a similar study at 180° C. oligomerization temperature to produce 12 cS (100° C.) HVI-PAO lubricant. It is clear from these data that the regeneration process of the instant invention can operate to allow repeated oligomerization cycles in the HVI-PAO process without loss in yield or product properties. Indeed, using regenerated catalyst prepared according to this invention surprisingly and unexpectedly improves the yield of lubricant compared to fresh catalyst when the two catalysts are compared with other oligomerization conditions, primarily temperature, held constant. This unique discovery indicates that the reduced chromium catalyst on silica support is a superior catalyst to freshly prepared catalyst when it is regenerated by the process of the instant invention.

The reduced chromium oxide on silica catalyst used in the present invention may be activated by the procedure described above, with either carbon monoxide or hydrogen as reducing agent. In regeneration of the catalyst, carbon monoxide or hydrogen may be used as well. In Example 8, catalyst activation is illustrated in comparison for both CO and $H_2$ reduction of chromium oxide on silica.

EXAMPLE 8

Two samples of 1.06% Cr on silica are calcined at 800° C. with air. Sample 1 is reduced with CO at 350° C. and sample 2 is reduced with $H_2$ at 300° C. The catalysts are tested for 1-hexene oligomerization at 60° C., as described before. The results are presented in Table 2.

TABLE 2

| Sample | 1 | 2 |
|---|---|---|
| lube yield, wt % | 84 | 12.5 |
| V @ 100° C., cS | 1882 | 737 |
| $(MW)_n$, $\times 10^3$ | 4.53 | 2.9 |
| $(MW)_w \times 10^3$ | 18.75 | 12.4 |
| $Q = (MW)_x/(MW)_n$ | 4.14 | 4.2 |

These results show that, while CO reduction is preferred, $H_2$ reduction is effective in providing an oligomerization catalyst.

While the invention has been described with preferred embodiments, the inventive concept is not limited except as set forth in the following claims.

What is claimed is:

1. In a process for the preparation of liquid hydrocarbons suitable as lubricant basestocks from alpha olefin feedstock containing 6 to 20 carbon atoms, or mixtures of such olefins, comprising contacting said olefins under oligomerization conditions, at reaction temperature between 90° to 250° C. to vary product viscosity, and with a chromium catalyst on a porous support, which catalyst has been treated by oxidation at a temperature of 200° C. to 900° C. in the presence of an oxidizing gas and then by treatment with a reducing agent at a temperature and for a time sufficient to reduce said catalyst to a lower valence state to obtain an oligomeric liquid lubricant composition comprising $C_{30}$–$C_{1300}$ hydrocarbons, said composition having a branch ratio of less than 0.19, weight average molecular weight between 420 and 45,000, number average molecular weight between 420 and 18,000, molecular weight distribution between 1 and 5 and pour point below −15° C., the improvement comprising; regenerating deactivated chromium catalyst under regenerating conditions in a process comprising the steps of:

(a) purging said deactivated catalyst with inert gas at elevated temperature and time sufficient to strip unreacted olefin and lubricant product;

(b) contacting said deactivated and purged catalyst with a stream of oxidizing gas while heating to elevated temperature at a rate and for a time sufficient to oxidize said catalyst and remove carbonaceous deposits;

(c) cooling said oxidized catalyst and contacting with a stream of reducing gas in an amount sufficient and at a temperature and for a time sufficient to reduce said oxidized catalyst to essentially lower valent chromium.

2. The process of claim 1 wherein step (b) oxidized catalyst comprises essentially hexavalent chromium.

3. The process of claim 1 wherein step (a) inert gas comprises nitrogen.

4. The process of claim 1 wherein said deactivated catalyst is purged at a temperature of between 20° and 200° C. for about one hour and a temperature between 200° and 600° C. for about 12 hours.

5. The process of claim 1 wherein said oxidizing gas comprises air.

6. The process of claim 1 wherein step (b) purged catalyst is heated from about 100° C. to 600° C. at a rate of about one degree celsius per minute and maintained at about 600° C. for about 12 hours.

7. The process of claim 1 wherein step (c) oxidized catalyst is cooled to about 350° C. and said reducing gas comprises carbon monoxide at a temperature of about 350° C.

8. The process of claim 1 wherein said liquid lubricant composition has a viscosity index greater than 130.

9. The process of claim 1 wherein the support comprises silica.

10. The process of claim 1 wherein the yield of said lubricant, oligomerized at the same reaction temperature, is greater using regenerated catalyst than using fresh catalyst.

11. A process for oligomerizing alpha olefins to produce lubricant range hydrocarbon including the steps of:

(a) contacting $C_6$–$C_{20}$ alpha olefin with a supported solid reduced metal oxide catalyst under oligomerization conditions at a temperature of about 90° to 250° C., said metal oxide comprising a lower valence form of at least one Group VIB metal to produce lubricant range hydrocarbon product having a branch ratio of about 0.10 to 0.19 and a viscosity index of at least about 130;

(b) regenerating deactivated reduced metal oxide catalyst under regenerating conditions in a process comprising the steps of:

(i) purging said deactivated catalyst with inert gas at elevated temperature and time sufficient to strip unreacted olefin and lubricant product;

(ii) contacting said deactivated and purged catalyst with a stream of oxidizing gas while heating to elevated temperature at a rate and for a time sufficient to oxidize said catalyst and remove carbonaceous deposits;

(iii) cooling said oxidized catalyst and contacting with a stream of reducing gas in an amount sufficient and at a temperature and for a time sufficient to reduce said oxidized catalyst to lower valence state catalyst.

12. The process of claim 11 wherein said metal oxide is chromium oxide; said support is silica, said reducing gas is taken from the group consisting of carbon monoxide and hydrogen; and said lower valence state catalyst is essentially lower valent chromium.

* * * * *